United States Patent [19]
Caillouette

[11] Patent Number: 6,083,178
[45] Date of Patent: *Jul. 4, 2000

[54] ESTROGEN OR ESTRADIOL NEED DETERMINATION BY VAGINAL ACIDITY DETERMINATION

[76] Inventor: James C. Caillouette, 685 Oak Knoll Cir., Pasadena, Calif. 91106

[ * ] Notice: This patent is subject to a terminal disclaimer.

[21] Appl. No.: 08/848,906

[22] Filed: May 1, 1997

Related U.S. Application Data

[60] Division of application No. 08/570,534, Dec. 11, 1995, Pat. No. 5,762,614, which is a continuation-in-part of application No. 08/537,379, Oct. 27, 1995, Pat. No. 5,577,512, which is a continuation-in-part of application No. 08/376,830, Jan. 23, 1995, Pat. No. 5,664,579, which is a continuation-in-part of application No. 08/295,399, Aug. 25, 1994, Pat. No. 5,425,377.

[51] Int. Cl.$^7$ .................................................. A61B 10/00
[52] U.S. Cl. ........................................... 600/572; 600/584
[58] Field of Search .................................. 604/1; 128/749, 128/759; 33/755, 758–760, 511, 512; 600/551, 572, 584

[56] References Cited

U.S. PATENT DOCUMENTS

| | | | |
|---|---|---|---|
| 3,037,496 | 6/1962 | Melges | 600/551 |
| 3,986,494 | 10/1976 | Preti | 600/551 |
| 4,013,066 | 3/1977 | Schuster | 600/551 |
| 5,063,930 | 11/1991 | Nucci | 606/191 |
| 5,147,288 | 9/1992 | Schiavo | 604/1 |

*Primary Examiner*—Michael A. Brown
*Attorney, Agent, or Firm*—William W. Haefliger

[57] ABSTRACT

In the method of determining need for human estrogen or estradiol level change, the steps include determining local acidity proximate a moist wall surface of the vagina, as differing from desired threshold level, and administering sufficient estrogen or estradiol to result in change in acidity toward such level.

20 Claims, 4 Drawing Sheets

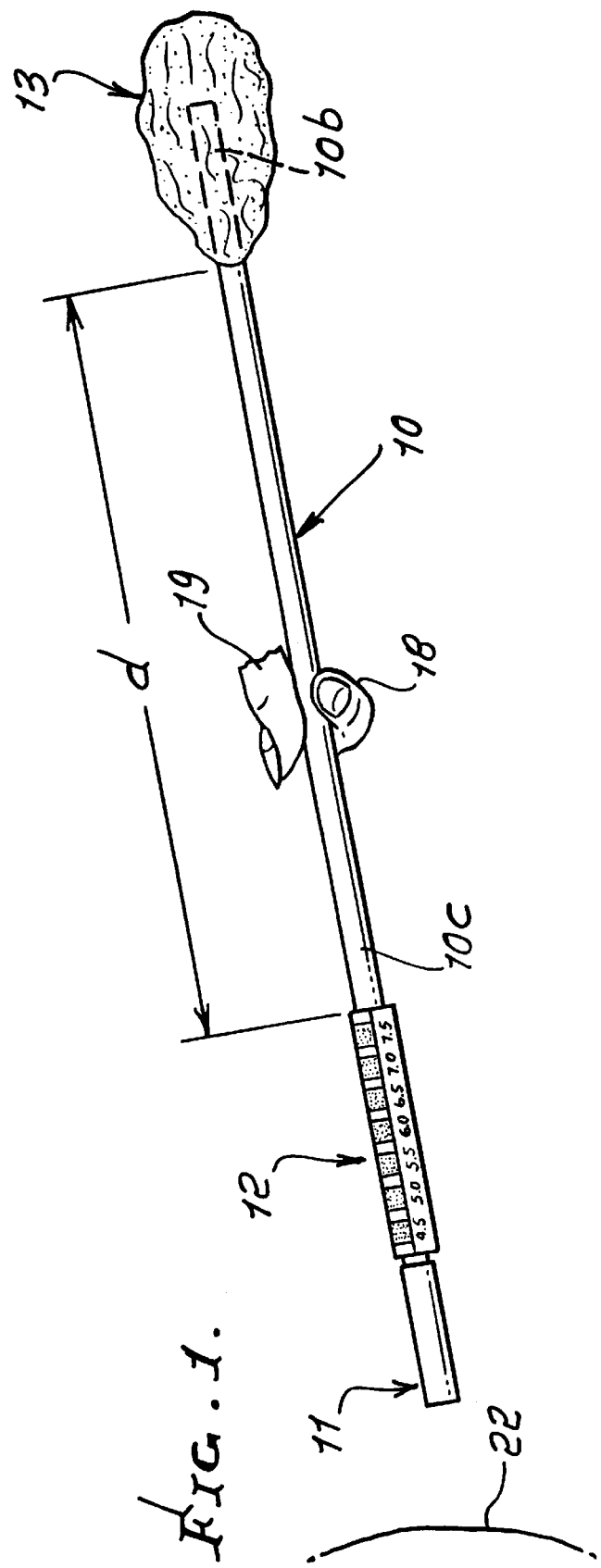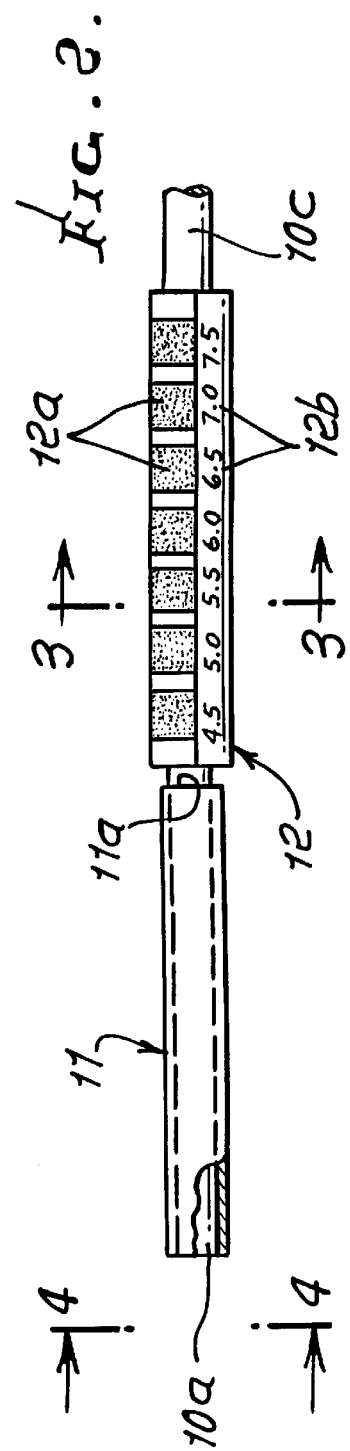

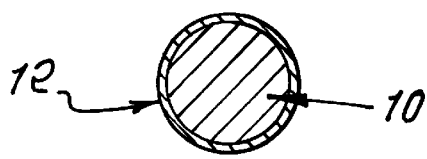
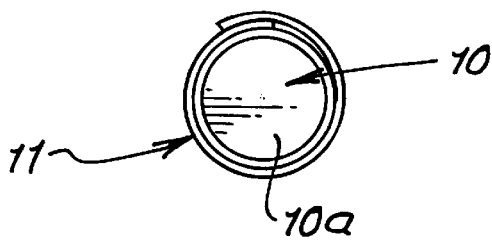
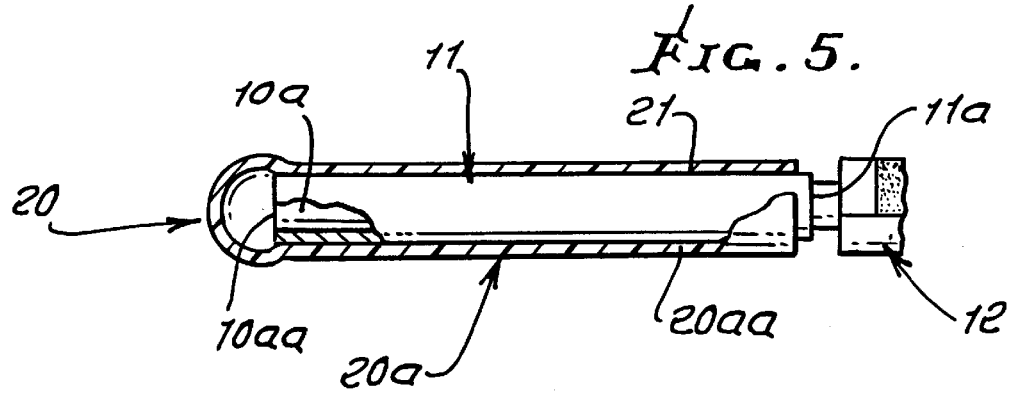
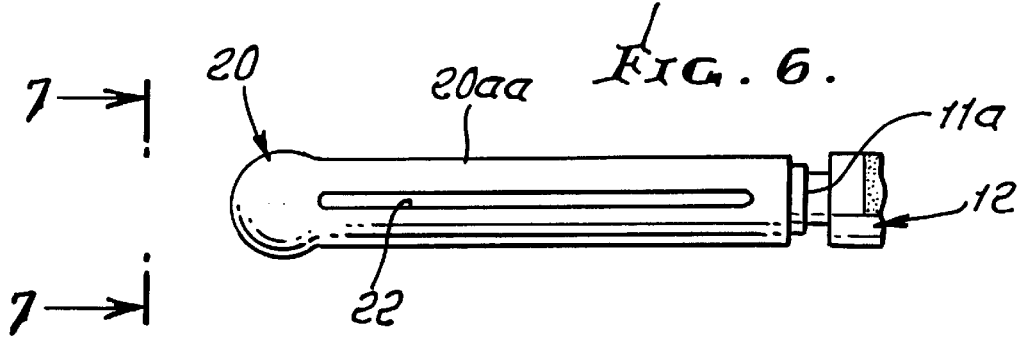
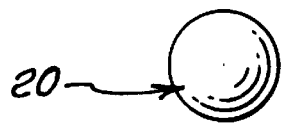

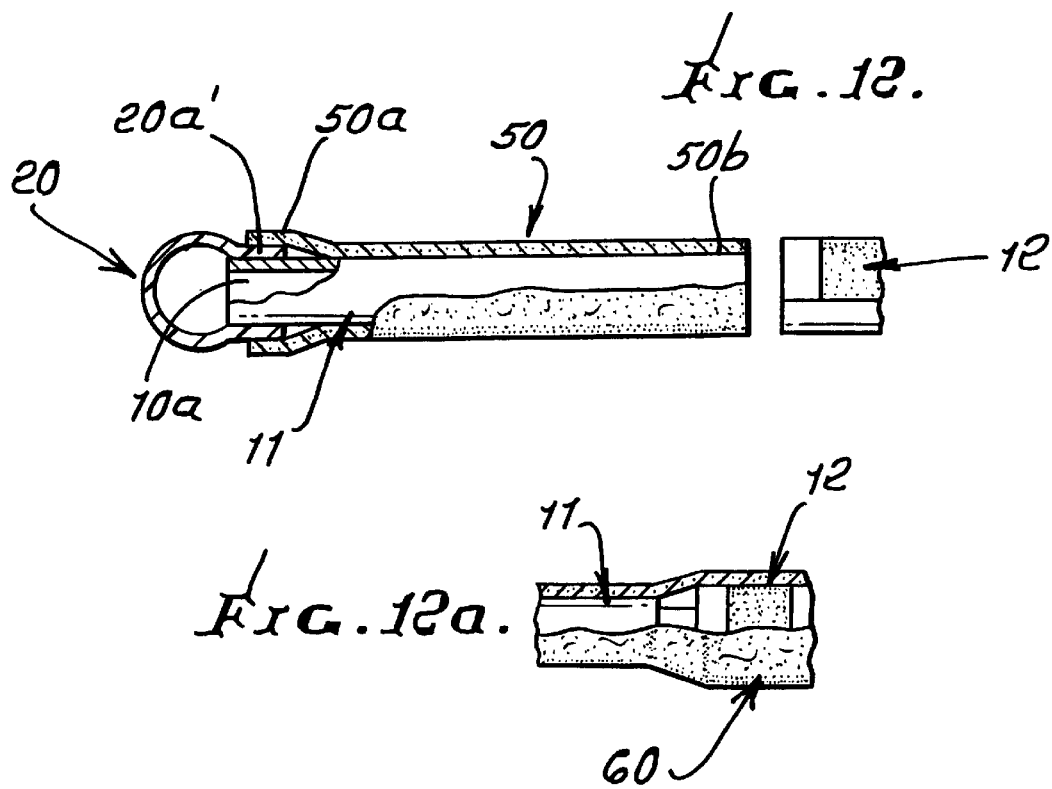
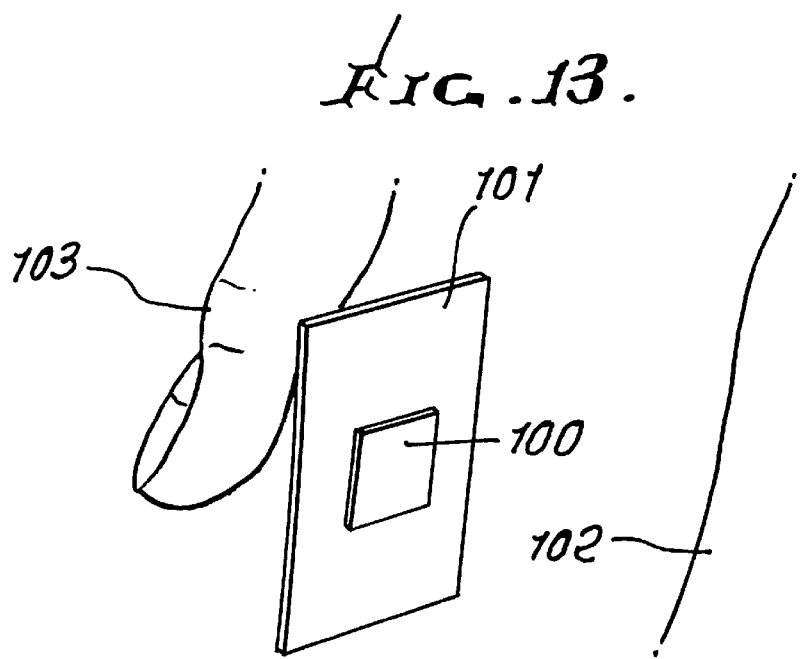

ESTROGEN OR ESTRADIOL NEED DETERMINATION BY VAGINAL ACIDITY DETERMINATION

This application is a divisional of prior U.S. Ser. No. 08/570,534, filed Dec. 11, 1995, now U.S. Pat. No. 5,762,614, which is a continuation-in-part of prior U.S. Ser. No. 08/537,379, filed Oct. 27, 1995, now U.S. Pat. No. 5,577,512, which is a continuation-in-part of prior U.S. Ser. No. 08/376,830, filed Jan. 23, 1995, now U.S. Pat. No. 5,664,579 which is a continuation-in-part of prior U.S. Ser. No. 08/295,399, filed Aug. 25, 1994 now U.S. Pat. No. 5,425,377.

BACKGROUND OF THE INVENTION

This invention relates generally to factors involved in determining estrogen or estradiol administration to human females, and more particularly to a simple and effective method and means to effect such determination such as need for changes in dosage of estrogen or estradiol.

There is need for improvements in methods to determine whether or not a human female should be administered higher or lower levels of estrogen or estradiol. The present invention addresses that need.

SUMMARY OF THE INVENTION

It has been discovered that the acidity level of a moist wall surface of the vagina can be employed in estrogen or estradiol need determination. In accordance with the invention, the method of determining need for estrogen or estradiol increase includes the steps:

a) determining local acidity proximate a moist wall surface of the vagina, as differing from desired threshold level, b) and administering sufficient estrogen or estradiol to result in change in acidity toward such level.

Typically, administering of sufficient estrogen or estradiol may be effected on a periodic regular basis, as for example increased or decreased dosage on a daily basis.

Another object is the carrying out of such determination of local acidity as by employing an acidity indicator, for contacting the wall surface of the vagina. Such an indicator may desirably include one of the following:

i) NITRAZINE® paper
ii) phenaphthazine on a carrier
iii) a material or materials exhibiting different colorations as a function of pH level.

A strip of material may be used to carry the indicator, and such a strip may be employed in contacting the vaginal wall. One method of use is to provide the strip of material on an applicator, an example being a carrier stick which is easily manipulable.

A further object is to provide a pH level indicator comprising a material or materials exhibiting colorations corresponding to pH levels of moisture of the wall surface of the vagina, said colorations being different for different pH levels. The desired threshold level of acidity is approximately 4.2.

Yet another object is to provide a method that includes the steps:

a) providing a pH detection means on a carrier stick,
b) providing a protective porous layer adjacent said pH detection means,
c) manipulating the stick to obtain pH detection of vaginal moisture, and including allowing vaginal moisture to penetrate said porous layer for contact with said pH detection means,
d) visually observing said detection means,
e) and determining from said pH detection a need for a change in estrogen or estradiol level to be administered to a human female.

These and other objects and advantages of the invention, as well as the details of an illustrative embodiment, will be more fully understood from the following specification and drawings, in which:

DRAWING DESCRIPTION

FIG. 1 is a side elevational view of stick apparatus incorporating the invention;

FIG. 2 is an enlarged side view of one end portion of the FIG. 1 stick apparatus;

FIG. 3 is an enlarged section taken on lines 3—3 of FIG. 2;

FIG. 4 is an enlarged end view taken on lines 4—4 of FIG. 2;

FIG. 5 is an elevation, partly in section, showing a modification;

FIG. 6 is a side elevation of the FIG. 5 modification;

FIG. 7 is an end view taken on lines 7—7 of FIG. 6;

FIG. 12 is a view like FIG. 8, showing a protective porous layer applied over a pH indication strip;

FIG. 12a is a view like FIG. 12, but showing the protective porous layer extending over the color comparison measurement means; and FIG. 13 is a perspective view showing pH indicator manipulation manually.

DETAILED DESCRIPTION

Figure 8:
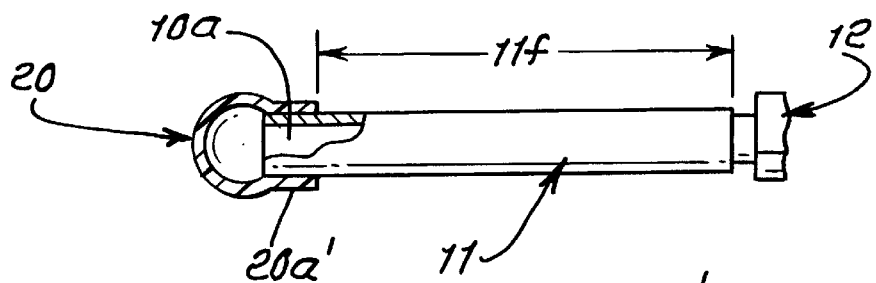
FIG. 8 is an elevation showing a further modification.

As referred to, the method of the invention concerns determining need for human estrogen or estradiol level change, through vaginal wall pH determination. Typical steps include:

a) determining local acidity proximate a moist wall surface of the vagina, as differing from desired threshold level, b) and administering sufficient estrogen or estradiol to result in change in said acidity toward said level.

A pH indicator 100, as seen in FIG. 13 may be employed, and that indicator may be located on a carrier strip 101, which is easily manipulable into contact with the vaginal wall, shown at 102, the user's finger shown at 103 to urge the tissue strip toward the wall surface. Such an indicator may take the form of one of the following, although other indicators are usable.

i) NITRAZINE® paper
ii) phenaphthazine on a carrier
iii) a material or materials exhibiting different colorations as a function of pH level.

The indicator may desirably exhibit different colorations corresponding to different pH levels, of moisture at the vaginal wall, and from which the observed coloration may be used to indicate need for greater or lesser estrogen or estradiol dosage, as on a daily or other periodic basis. In the case of NITRAZINE® paper (phenaphtazine), the correlation of pH to color is as follows:

| pH  | Color        |
|-----|--------------|
| 4.5 | golden yellow |
| 5.0 | beige        |
| 5.5 | light olive  |
| 6.0 | dark olive   |
| 6.5 | olive blue   |
| 7.0 | purple blue  |
| 7.5 | dark blue    |

In a typical example, if the user detected or determined an indicator color of dark olive, it would be determined that an estrogen or estradiol increase of about 50% above the existing daily level of use would be recommended, in order to diminish pH level to 4.2 to 4.5 within one to two weeks, for example. Testing would be performed on a once a week basis. Thus, if the user had been taking 1 mg. of estrogen per day, she would be recommended to increase that level to 1.5 mg. per day, the objective being to reduce the pH level to about 4.5 within about one week. If the tested color were not golden yellow (4.5 pH) after 7–8 days, the dosage might be increased to 2.0 mg. level, per day, until golden yellow of the test strip was achieved. Thus, pH determination is indicative of need for change in estrogen or estradiol dosage (up or down).

The indicator may alternatively be employed on a manipulable apparatus, as for example a carrier stick. In FIGS. 1–4, an elongated, narrow carrier stick 10 may consist of wood, plastic, or other material. Provided on the carrier stick are:

a pH indication means, as generally shown at 11, at one end portion 10a of the stick; and a color comparison pH measurement means, as generally indicated at 12, spaced from stick end portion 10a, but close to 11;

As shown, the first means 11 may comprise a pH indication strip, such as a NITRAZINE® strip, wound about the stick end portion 10a and adhered to same as by an adhesive. NITRAZINE® strips are products of Squibb. The color comparison pH measurement means 12 may comprise a thin paper strip adhered to the stick surface to extend lengthwise of the stick from the edge or end 11a of the first means 11. The second means is shown to have color gradations in a series sequence, as in colored bands 12a, positioned lengthwise of or along the stick. In addition, the paper strip 12 may include pH numerical indicators 12b along side the color gradation bands, to enable:

visual color comparison of the pH indication means 11 (immediately after its exposure to vaginal fluid) with the bands 12a, for visual selection of that band most close in color to the color of the indication means 11;

and immediate visual readout of the pH number adjacent the selected band.

Such readout of pH is then compared with the desired level of about 4.2 to enable determination of a recommended dosage of estrogen or estradiol, as on a daily basis.

The stick projects freely at 10c away from the first and second means 11 and 12 for manual manipulation (see the grasping finger and thumb 18 and 19), to first obtain pH indication of vaginal wall moisture at one end of the stick, and to enable visual interpretation of that indication by color comparison with the second means, without manual release of the stick. The stick is then disposable, or may be disposed of.

Lengthwise spacing "d" between 12 and stick end 10d is such as to enable free manual manipulation of the stick; and such spacing is typically between 3 and 5 inches, enabling ready finger grasping of the stick and manipulation thereof. In a specific example, "d" is about 4 inches, and the stick diameter or width is about ⅜ inch.

The method of measuring pH of vaginal moisture includes the steps:

a) providing a pH indicator on a carrier stick, b) manipulating the stick between its opposite ends to obtain pH indication of vaginal wall moisture at said indicator, c) visually interpreting that indication to determine need for a change in estrogen or estradiol dosage, d) and disposing of the stick, The overall sizes of 11, 12 and 13 are such as to enable ready insertion into the vagina, via stick manipulation at zone 10c.

Referring now to the modification shown in FIGS. 5–7, a smooth surfaced protective tip 20 is provided to face endwise at the end 10aa of the stick end portion 10a. As shown, the tip 20 is endwise convex, as for example bulbous, to provide for or enable comfortable insertion of the stick end portion 10a into the vagina, for pH measurement. The tip 20 may typically be formed integrally with a sleeve 20a assembled over and closely fitting the measurement strip 11, and may be suitably adhered thereto, locally, as at 21. A suitable bonding agent is epoxy. The remainder of the strip 11 is therefore available for pH indication. Alternatively, the sleeve may be attached, as by heat shrinking, or by wedge fit.

A fluid access opening is provided through the wall of the sleeve, whereby vaginal moisture or fluid may access the strip 11 via that opening. See for example elongated slot 22 in the sleeve wall 20aa. The sleeve and tip may consist of transparent, molded, plastic material, to facilitate viewing of a change of color of the strip 11.

In FIG. 8, the sleeve 20a is shortened and attached at sleeve end 20a' into flush, or near flush, relation with the surface of the strip, at a locus on stick end portion 10a. This leaves the remaining length 11f of the strip openly exposed for moisture contact.

Figure 9:
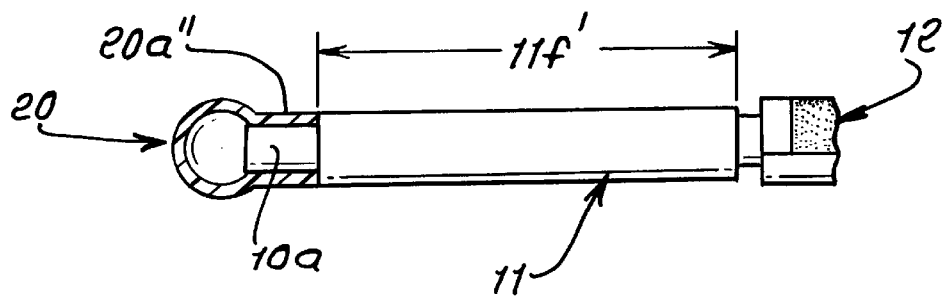
FIG. 9 is an elevation showing yet another modification.

In FIG. 9, the sleeve 20a" is also shortened and attached to the stick end portion 10a, and in endwise alignment with the strip 11. This also leaves the remaining length 11f' of the strip openly exposed for moisture contact.

Figure 10:
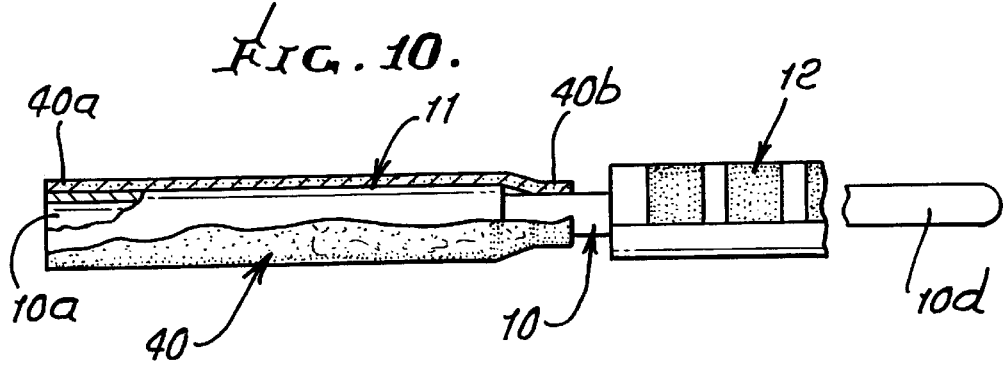
FIG. 10 is a view like FIG. 2, showing a protective porous layer applied over a pH indicator strip.

Referring now to the modification seen in FIG. 10, the elements the same as in FIG. 2 are given the same numerals. In addition a protective layer 40 in the form of a thin porous barrier, is applied adjacent the outer side of strip 11 so as to cover the latter (i.e. extend thereabout) and to be carried by the stick. Layer 40 allows vaginal moisture to penetrate through it and to contact the pH indicator strip 11, as during a test. Following the test, the strip 11 may be observed as described above, and for this purpose the layer 40 may be at least partly removed from adjacency to the strip, as by complete manual removal. Opposite end portions 40a and 40b of layer 40 may be initially attached as by light bonding or sticking to the ends of the strip 11, or to the stick, allowing pull-away removal of the layer at the end of the test. Such bonding agents are known, as on 3M Micropore Tape. Layer 40 acts as a barrier, during a test, to block direct contact of vaginal tissue with strip 11, preventing any possible irritation of such tissue.

Figure 11:
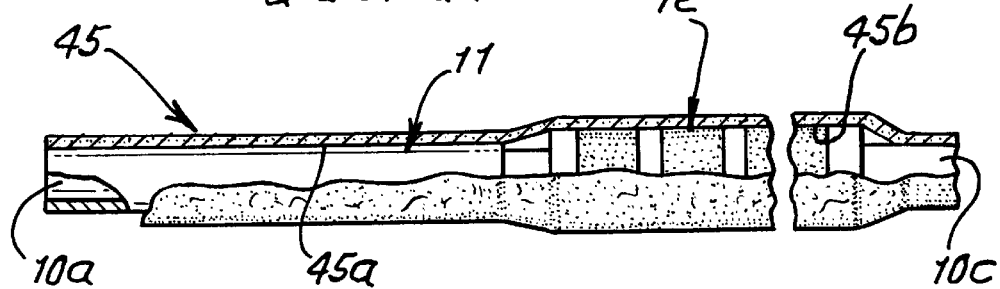
FIG. 11 is a view like FIG. 10, but showing the protective layer also applied over the color comparison measurement means.

In FIG. 11, the elongated layer 45 is like layer 40, but also extends over and about the color comparison measurement means 12, and is adhered, as described above, to the elements 11 and 12, as at 45*a* and 45*b* to completely cover 11 and 12 as during a test, while allowing pull-away of the layer 45 for visual observation of 11 and 12 after the test. Either one or both of 11 and 12 may be considered as a pH detecting means.

FIG. 12 is like FIG. 8, but layer 50 corresponding to layer 40 has its end 50*a* adhered to and about the sleeve 20*a*', while end portion 50*b* is adhered to the right end of strip 11, as shown. Note smooth surfaced blunt knob 20, as referred to above.

FIG. 13 is like FIG. 12, except that the layer 60, corresponding to 50, is elongated to cover the color comparison measurement means 12, and to adhere at 60*b* to the rightward end of 12.

In FIGS. 10–13, the porous barriers, as at 40, 45, 50 and 60 may consist of one or more barrier tissue layers, as for example are used in incontinence pads. One example is the outer layer of the Kimberly Clark product NEW DEPEND. Another usable barrier is the 3M product known as MICROPORE tape. One side of such tape is "tacky", i.e. weakly adhesive, so that it will adhere along the tape length to the elements 11 and/or 12 referred to. Barriers 45 and 50 as referred to may comprise such tape material.

I claim:

1. In the method of detecting pH of vaginal moisture, the steps that include:
    a) providing a pH detection means on a carrier stick,
    b) providing a protective porous layer adjacent said pH detection means,
    c) manipulating the stick to obtain pH detection of vaginal moisture, and including allowing vaginal moisture to penetrate said porous layer for contact with said pH detection means,
    d) visually observing said detection means,
    e) and determining from said observed pH detection means a need for a change in estrogen or estradiol level to be administered to a human female.

2. The method of claim 1 including removing said porous layer from adjacency to said pH detection means to allow said visually observing of said detection means.

3. The method of claim 1 including providing said pH detection means to include at least one of the following:
    i) a pH indicating strip
    ii) a color comparison measurement means.

4. In apparatus for measuring pH of vaginal moisture for determination of need for change in estrogen or estradiol dosage, the combination comprising:
    a) an elongated carrier stick,
    b) pH indicating means on the stick, at one end portion thereof, and sized for application to a zone adjacent the wall of the vagina.

5. In apparatus for measuring pH of vaginal moisture for determination of need for a change in estrogen or estradiol dosage, the combination comprising:
    a) an elongated carrier stick,
    b) pH indicating first means in the form of a strip on the stick, at one end portion thereof,
    c) color comparison pH measurement second means on the stick, spaced from said one end portion thereof,
    d) the stick projecting freely from said first and second means for manual manipulation to first obtain pH indication of vaginal moisture at said one end of the stick, and to enable visual interpretation of that indication by color comparison with said second means, without manual release of the stick,
    e) the stick then being disposable to dispose of both said first and second means in one disposal step,
    f) there being a protective porous layer extending adjacent at least one of the following:
        $x_1$) said strip
        $x_2$) said color comparison measurement means.

6. The apparatus of claim 5 wherein said strip is adhered to said one end of the stick, and said second means extends lengthwise along the stick, away from said first means.

7. The apparatus of claim 6 wherein said second means has color gradations in a series sequence lengthwise along the stick.

8. The apparatus of claim 7 wherein said strip extends about the stick.

9. The apparatus of claim 8 wherein said strip is wound about the stick at said one end thereof.

10. The apparatus of claim 7 wherein there are pH numerical indications on the stick, in close association with said color gradations.

11. The apparatus of claim 5 including a smooth surfaced protective tip facing endwise at said one end of the stick.

12. The apparatus of claim 1 wherein said tip has bulb shape.

13. The apparatus of claim 11 including a protective plastic sleeve extending about a portion of said stick in endwise alignment with said strip, said sleeve carrying said tip.

14. The apparatus of claim 8 wherein said porous layer has a portion thereof adhered to the stick.

15. The apparatus of claim 5 wherein said porous layer terminates at a location characterized in that a substantial length of the strip remains freely and openly exposed outwardly.

16. In apparatus for detecting pH of vaginal moisture, the combination comprising
    a) an elongated stick
    b) pH detecting means on the stick, at one end portion thereof,
    c) and a protective porous layer extending adjacent said pH detecting means.

17. The combination of claim 16 wherein said protective porous layer has a portion thereof attached to the stick.

18. The combination of claim 16 wherein said pH detecting means includes at least one of the following:
    i) a pH indicating strip
    ii) a color comparison measurement means.

19. The combination of claim 16 including a smooth surfaced protective tip facing endwise at said one end of the stick.

20. In the method of detecting pH of vaginal moisture, the steps that include:
    a) providing a pH detection means on a carrier stick,
    b) providing a protective porous layer adjacent said pH detection means,
    c) manipulating the stick to obtain pH detection of vaginal moisture, and including allowing vaginal moisture to penetrate said porous layer for contact with said pH detection means,
    d) and visually observing said detection means, for determining need for a change in estrogen or estradiol dosage.

* * * * *